US009549955B2

(12) United States Patent
Rittmann et al.

(10) Patent No.: US 9,549,955 B2
(45) Date of Patent: Jan. 24, 2017

(54) REDUCING SHORT-CHAIN FATTY ACIDS AND ENERGY UPTAKE IN OBESE HUMANS BY MANAGING THEIR INTESTINAL MICROBIAL COMMUNITIES

(71) Applicant: ARIZONA BOARD OF REGENTS FOR AND ON BEHALF ,OF ARIZONA STATE UNIVERSITY, Tempe, AZ (US)

(72) Inventors: Bruce Edward Rittmann, Tempe, AZ (US); Rosa Krajmalnik-Brown, Chandler, AZ (US); Husen Zhang, Tempe, AZ (US); John Dibaise, Scottsdale, AZ (US); Michael Crowell, Fountain Hills, AZ (US)

(73) Assignee: Arizona Board of Regents for and on behalf of Arizona State University, Tempe, AZ (US)

( * ) Notice: Subject to any disclaimer, the term of this patent is extended or adjusted under 35 U.S.C. 154(b) by 252 days.

(21) Appl. No.: 14/204,757

(22) Filed: Mar. 11, 2014

(65) Prior Publication Data
US 2014/0193372 A1   Jul. 10, 2014

Related U.S. Application Data

(63) Continuation of application No. 13/579,326, filed as application No. PCT/US2011/024985 on Feb. 16, 2011, now abandoned.

(60) Provisional application No. 61/304,944, filed on Feb. 16, 2010.

(51) Int. Cl.
| | |
|---|---|
| *A61K 35/74* | (2015.01) |
| *A61K 35/741* | (2015.01) |
| *A61K 31/135* | (2006.01) |
| *A61K 31/185* | (2006.01) |
| *A61K 31/405* | (2006.01) |
| *A61K 45/00* | (2006.01) |

(52) U.S. Cl.
CPC .......... *A61K 35/741* (2013.01); *A61K 31/135* (2013.01); *A61K 31/185* (2013.01); *A61K 31/405* (2013.01); *A61K 35/74* (2013.01); *A61K 45/00* (2013.01)

(58) Field of Classification Search
None
See application file for complete search history.

(56) References Cited

U.S. PATENT DOCUMENTS

2006/0147496 A1* 7/2006 Lin .................. A61K 38/54
424/439
2008/0113003 A1   5/2008 Classen et al.

OTHER PUBLICATIONS

Cani et al., Changes in gut microbiota control inflammation in obese mice through a mechanism involving GLP-2-driven improvement of gut permeability, Gut, 2009, vol. 58, pp. 1091-1103.*
San et al., 3rd International Immunonutrition Workshop Session 8: Probiotics in the defence and metabolic balance of the organism Gut microbiota in obesity and metabolic disorders, Proceedings of the Nutrition Society, Presented in Spain 2009, vol. 69, pp. 434-441.*
Cummings et al., Prebiotic digestion and fermentation, American Journal of Clinical Nutrition, 2001, vol. 73 (suppl), pp. 415S-420S.*
Renilla et al., Acetate scavenging activity in *Escherichia coli*: interplay of acetyl-CoA synthetase and the PEP-glyoxylate cycle in chemostat cultures, Applied Microbial and Cell Physiology, 2012, vol. 93, pp. 2109-2124.*
Membrez et al., Gut microbiota modulation with norfloxacin and ampicillin enhances glucose tolerance in mice, The FASEB Journal, 2008, vol. 22, pp. 2416-2426.*
Schink, Bernard, "Energetics of Syntrophic Cooperation in Methanogenic Degradation", Microbiology and Molecular Biology Reviews, 1997, 61(2), pp. 262-280.
Dibaise, et al, "Gut Microbiota and Its Possible Relationship with Obesity", Mayo Clinic Proceedings, 2008, 83(4).
Zhang et al, "Human Gut Microbiota in Obesity and After Gastric Bypass", Pnas, 2009, 106(7), pp. 19-39.
International Search Report mailed Nov. 30, 2011 issued in PCT/US11/24985.
Drake et al, Acetogenic Prokaryotes, Prokaryotes, 2006, vol. 2, pp. 354-420.

* cited by examiner

*Primary Examiner* — Louise W Humphrey
*Assistant Examiner* — Christopher Keller
(74) *Attorney, Agent, or Firm* — Nixon Peabody LLP; Janet Garetto; Leena H. Karttunen Contarino

(57) ABSTRACT

The present invention provides for microbial compositions and methods for reducing the concentration of short-chain fatty acids in the gut as a way to reduce energy uptake and manage obesity. More specifically, the invention provides for decreasing short-chain fatty acids available for absorption in the human gut, such as acetate, using one or more of: a probiotic including a homo-acetogenic, acetate oxidizing bacterium that converts acetate to $H_2$; a probiotic including an acetoclastic methanogen; a microbial electrolysis cell comprising a homo-acetogenic bacterium and/or an acetoclastic methanogen; a prebiotic that enhances the growth or function of acetate-scavenging microbiota; or a highly selective antibiotic that targets $H_2$-oxidizing methanogens.

3 Claims, 1 Drawing Sheet

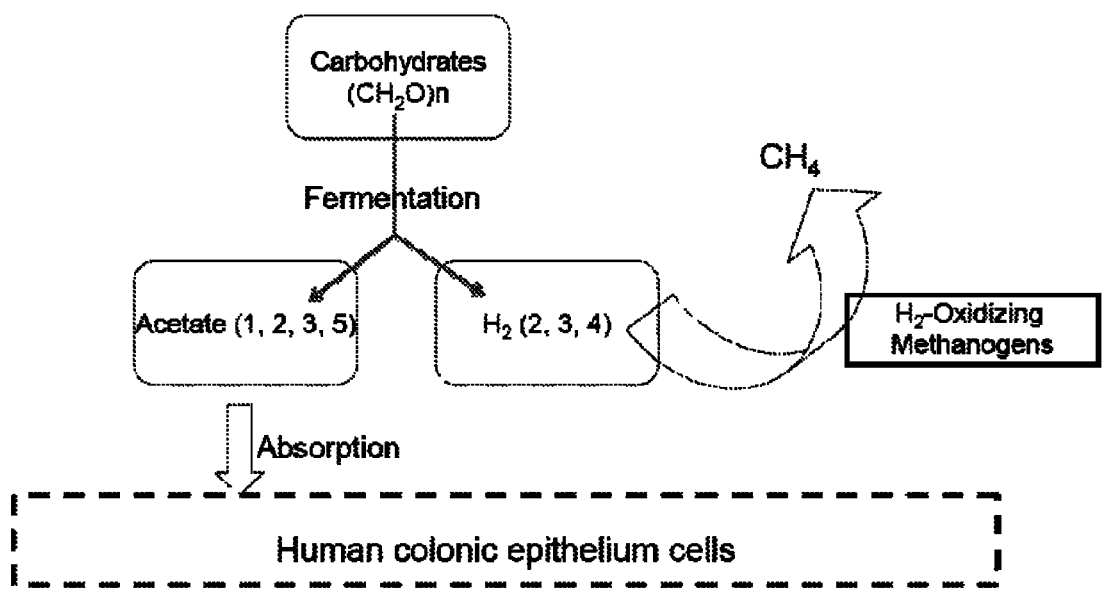

REDUCING SHORT-CHAIN FATTY ACIDS AND ENERGY UPTAKE IN OBESE HUMANS BY MANAGING THEIR INTESTINAL MICROBIAL COMMUNITIES

RELATED APPLICATIONS

This is a continuation application of U.S. Ser. No. 13/579,536, filed on May 21, 2013, which is a 371 National Stage Application of PCT/US11/24985, filed on Feb. 16, 2011, which claims the benefit of U.S. Ser. No. 61/304,944, filed 16 Feb. 2010, incorporated fully herein by reference.

FIELD OF THE INVENTION

The present invention relates to microbiology and the manipulation of intestinal microbiota to modify dietary energy uptake in a human subject. More specifically, the present invention provides means and techniques to scavenge short-chain fatty acids, such as acetate, before they are absorbed in the gut.

BACKGROUND

Obesity is epidemic in the U.S. and growing in much of the developed world. The health-care costs associated with obesity and obesity-related diseases (e.g., diabetes and other metabolic disease) are enormous and growing in proportion to the epidemic. The current means to reverse obesity is surgical: gastric bypass or gastric banding. Both means are invasive, expensive, risk numerous adverse events, and may leave permanent sequelae. There is a need for simple, non-invasive means to inhibit, reverse or prevent obesity.

SUMMARY

The present invention provides for the use of one or more microbiologically-based means to decrease intestinal net fatty acid (e.g., acetate) concentration so that its absorption is decreased, such that the subject's net energy uptake declines. Rapid $H_2$ oxidation by methanogens accelerates the bacterial fermentation of carbohydrates. In the human intestine, the removal of $H_2$ by methanogens leads to increased production of short-chain fatty acids, such as acetate, proprionate and butyrate, which are absorbed through the intestinal wall. Rapidly scavenging acetate, lowering the production of short-chain fatty acids, or both, decreases caloric uptake by the human host through the intestine. An aspect of the present invention diverts acetate from absorption by managing interspecies $H_2$ and acetate transfer among Bacteria and Archaea and by scavenging acetate, thus affecting energy uptake by the human host.

Another aspect of the present invention provides for compositions for decreasing acetate in the gut comprising a probiotic agent comprising acetoclastic methanogens and/or selected homo-acetogens. Another aspect provides for a miniature microbial electrolysis cell that converts acetate into $H_2$.

Other aspects of the invention provide for methods for reducing acetate in the gut by administering acetoclastic methanogens as a probiotic agent; administering selected homo-acetogens as a probiotic agent; planting a miniature microbial electrolysis cell that converts acetate into $H_2$; or combining one or more of these steps, optionally with antibiotic therapy, or other approaches to obesity management.

DESCRIPTION OF THE DRAWINGS

FIG. 1 is a schematic of methods to modulate energy absorption by managing the microbial community in the intestines. Fermentation of organic compounds (represented as 'Carbohydrates') produces $H_2$ and acetate as key products. Acetate can be absorbed rapidly by the host through colonic epithelium cells and converted to fat. In non-obese individuals, the degree of fermentation appears to be controlled by the build up of $H_2$, which creates a thermodynamic roadblock in acetate-producing fermentation. In obese individuals, $H_2$-oxidizing methanogens consume the $H_2$ and clear the roadblock so that more acetate is formed and absorbed by the host. Embodiments of the present invention include one or more means and techniques to consume the acetate before it is absorbed and, in some cases, suppress the $H_2$-oxidizing methanogens. For example, embodiments include (1) administering acetoclastic methanogens as a probiotic agent; (2) administering selected homo-acetogens as a probiotic agent; (3) planting a miniature microbial electrolysis cell that converts acetate into $H_2$; (4) administering antibiotics to eliminate $H_2$-utilizing methanogens; or (5) a combination of (1) through (4). Note that approaches (1) through (3) scavenge acetate before it is absorbed by the host; approaches (2) and (3) also produce $H_2$, which slows acetate production by accentuating the thermodynamic roadblock; and approach (4) reduces the consumption of $H_2$, which slows acetate production by accentuating the thermodynamic roadblock.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Recent evidence suggests that the gut microbial community may play a role in obesity by increasing or decreasing the host's energy-harvesting efficiency. It is of high value to identify specific microbial lineages that play important roles in the development of obesity and to manage the microbial community for reducing obesity. It was found recently that the gut microbial community of obese individuals uniquely contains $H_2$-oxidizing methanogenic Archaea. Zhang et al., 106 P.N.A.S. 2365 (2009). Obese individuals also contained Prevotellaceae (phylum Bacteroidetes), which are know to ferment carbohydrates to acetate and $H_2$. The presence of both microorganisms in obese individuals creates a syntrophy that can lead to increased energy uptake by the human host. Specifically, $H_2$ uptake by these methanogens relieves a thermodynamic bottleneck for the fermentation that forms more acetate, which is then absorbed across the intestinal epithelium (as energy uptake). Hence, some embodiments of the present invention utilizes microbes that convert acetate into methane (i.e., acetoclastic methanogenesis) or that form $CO_2$ and $H_2$ from acetate (i.e., reverse homo-acetogenesis mediated by homo-acetogens).

Some embodiments of the present invention modulate syntrophy: a biological relationship in which microorganisms of two different species or strains are mutually dependent on one another for nutritional requirements. Anaerobic fermentation/methanogenesis is an example of a syntrophic relationship between different groups of microorganisms. Although fermentative bacteria are not strictly dependent on syntrophic relationships, they benefit from the activities of the $H_2$-scavenging organisms, because lower $H_2$ pressure makes the fermentation process more thermodynamically favorable. Dolfing & Tiedje, 54 Appl. Environ. Microbiol. 1871 (1988); Schink, 61 Microbiol. Mol. Bio. Rev. 262 (1997).

Acetogenic Bacteria and methanogenic Archaea are the two groups of microorganisms living in syntrophy during methanogenesis in the gut. Some fermentation products such as fatty acids longer than two carbon atoms, alcohols longer than one carbon atom, and branched-chain and aromatic fatty acids, can not be used directly in methanogenesis. In the acetogenesis process, these products are fermented to acetate and $H_2$ by obligate proton-reducing bacteria in syntrophic relationship with $H_2$-oxidizing methanogenic Archaea. This syntrophy exists because the consumption of $H_2$ by the methanogens creates low $H_2$ partial pressure that makes the acetogenic fermentation thermodynamically favorable. Similar syntrophy occurs with fermenting bacteria that produce $H_2$ and other short-chain fatty acids, such a propionate and butyrate. This syntrophy allows greater production of short-chain fatty acids that can then be absorbed across the intestinal epithelium. Zhang et al., 2009; Schink, 1997; Stams et al., 52 Water Sci. Technol. 13 (2005).

Modifying the intestinal microbiota provides a means to scavenge acetate before it can be taken up by the human host, as a means of obesity management. In some cases, the modifications also reduce production of the short-chain fatty acids in the intestines as an added method of managing obesity. In other words, the present invention is focused on reducing the concentrations of readily absorbed fermentation products in the gut as a means to lower energy uptake. Conversely, acetate accumulation may be enhanced in individuals in need of increased energy uptake.

The present invention provides for methods to manage the microbial community in the intestines in a way that diverts acetate before it is absorbed by the host and, in some cases, suppresses fatty acid production by fermenters. An example embodiment that achieves these goals comprises administering to a subject a composition comprising acetoclastic methanogens, such as *Methanosaeta soehngenii* and sp. (formerly *Methanothrix soehngenii*) and *Methanosarcina barkeri*, because these microorganisms can scavenge acetate before it can be absorbed by colonic epithelial cells. Based on stoichiometry, each mole of acetate consumed by these methanogens produces one mole of methane ($CH_4$) and one mole of carbon dioxide ($CO_2$), which are then expelled naturally as flatulence or through transfer to the bloodstream and lungs. These organisms can be produced in culture, see, e.g., Bryant, 25 Am. J. Clin. Nutr. 1324 (1972); Dubach et al., 30 Applied Microbiol. Biotech. 201 (1989). Obligate acetoclastic methanogens, such as *Methanosaeta soehngenii*, are ideal probiotic agents for the purpose of lowering the acetate concentration in the gut, because these microorganisms can not oxidize $H_2$.

Another embodiment of the present invention provides for administering a composition comprising homo-acetogenic bacteria that are capable of converting acetate to $H_2$ and $CO_2$. Examples include *Clostridium ultunense* and *Thermoacetogenium phaeum* strain PB. These microorganisms can scavenge acetate before it can be absorbed by colonic epithelial cells. Based on stoichiometry, each mole of acetate consumed by acetate-consuming homo-acetogenic bacteria produces four moles of $H_2$ and two moles of $CO_2$, which are naturally expelled as flatulence or through transfer to the bloodstream and lungs. In addition to consuming acetate before it is absorbed, the acetate-consuming metabolism of homo-acetogens produces $H_2$, which has the added benefit of producing $H_2$, which increases the thermodynamic roadblock to fermentation and the production of short-chain fatty acids (e.g., acetate). *Clostridium ultunense* can be grown in culture (Schink et al., 154 FEMS Microbiol. Letts. 331 (1997)).

Acetoclastic methanogens and homo-acetogenic bacteria are strict anaerobes. Thus, compositions comprising probiotics may use a delivery system, such as controlled-release capsules or microcapules, to deliver the bacteria through the upper digestive tract and into the intestines without exposure to oxygen. See U.S. Pat. No. 6,627,223; Saulnier et al., 20 Curr. Opin. Biotech. 135 (2009). Alternatively, a tablet comprising compressed probiotics can be formulated such that, although some bacteria perish in the upper gastrointestinal tract, sufficient numbers survive to the lower intestine to accomplish acetate scavenging and/or reduction. Such technologies are well known in the art. See Muller et al., *Manufacture of Probiotic Bacteria*, in PREBIOTICS & PROBIOTICS SCIENCE & TECH. (Springer Pub., NY, 2009).

Another embodiment administers a miniaturized microbial electrolysis cell (MEC), in which anode-respiring bacteria (ARB) oxidize acetate at the anode before acetate can be absorbed by the colonic epithelium cells. The MEC comprises a biofilm growing on the anode of a fuel cell. The biofilm contains ARB that oxidize acetate and transfers the electrons to the anode. Electrons move through an electrical connection to the cathode, where they reduce protons ($H^+$) to produce $H_2$. See Rittmann, 100 Biotech. Bioeng. 203 (2008); Torres et al., 77 Appl. Micro. Biotech. 689 (2007). An example acetate-fed MEC consortium included $\beta$-, $\delta$-, $\gamma$-Proteobacteria, Bacteroidetes, Firmicutes, and members of the order Rhodocyclaceae and Burkholderiaceae (*Azospira* sp., *Acidovorax* sp., and *Comamonas* sp.). Borole et al., 48 Biochem. Eng. J. 71 (2009). Based on stoichiometry, each mole of acetate consumed by the anode-respiring bacteria generates four moles of $H_2$ gas that can be expelled as flatulence or through transfer to the bloodstream and lungs. In addition to consuming acetate before it is absorbed, the acetate-consuming metabolism of a MEC has the added benefit of producing $H_2$, thus increasing the thermodynamic roadblock to fermentation and production of short-chain fatty acids such as acetate.

Another embodiment provides for the ingestion of prebiotics in the form of non-digestible foods that support the growth and metabolism of the acetate-scavenging microorganisms described herein.

Another embodiment provides for the additional step of ingesting agents (such as antibiotics) that affect the microbiota of the gut. For example, the antibiotic may be highly specific for $H_2$-consuming methanogens: a methanogen inhibitor that inhibits hydrogenotrophic methanogens and not acetoclastic methanogens. Other agents that target specific enzymes or pathways of hydrogenotrophic methanogens include iRNAs and small molecules. Alternatively, broad-spectrum antibiotics of may be used where probiotics are reintroduced either concurrently, regularly, or subsequently to replace the bacteria killed by the antibiotics. An example antibiotic is the semisynthetic, rifamycin-based, non-systemic antibiotic rifaximin (XIFAXAN®, Salix Pharmaceuticals, Inc., Morrsiville, N.C.), that is essentially non-absorbed from the gut and is being employed for certain gastrointestinal problems. The antibiotic therapy may be long-term or short-term, depending on the maintenance or establishment of the desired microbiota, or the obesity management goals of the subject in consultation with the physician. The efficacy of this step may be monitored by known laboratory and clinical techniques, and may be adjusted accordingly. This approach prevents the consumption of $H_2$ and increases the thermodynamic roadblock to fermentation and production of short-chain fatty acids.

The compositions and approaches discussed herein can be applied singly, in combination, or with other therapies designed to assist in weight reduction or metabolic modulation. FIG. 1 shows a schematic drawing of the syntrophic system of embodiments of the present invention, and how each of strategy works to counteract the absorption of short-chain fatty acids (e.g., acetate).

Thus, the present invention uses one or more of the foregoing microbiological compositions and approaches for managing the microbial ecology in the intestine to decrease absorption or short-chain fatty acids so that the subject's net energy uptake declines and obesity is reversed or prevented. The present invention diverts acetate away from gut absorption and/or reduces $H_2$ oxidation by methanogens. The approach is novel, because it exploits the recent discoveries that $H_2$-oxidizing methanogens play a role in promoting obesity by increasing acetate production from fermentation, while acetate-scavenging microorganisms can reduce acetate otherwise absorbed through the intestinal wall. It also is novel because it exploits a strategy of managing the microbial ecology in the human intestines to affect the concentration and absorption of short-chain fatty acids.

In conclusion, although diet and exercise ought to be effective for preventing obesity, much of the developed world is experiencing an epidemic of obesity. Current means to reverse obesity are surgical gastric bypass or gastric banding, which are invasive and expensive. The present invention does not require surgery or other invasive means to accentuate the positive effects of diet and exercise to prevent or reverse obesity. Additionally, should a surgical procedure be performed, the present invention can be used to improve the chances for a successful outcome, for example as an adjunct to gastric bypass.

The present invention may be defined in any of the following numbered paragraphs:

1. A composition for decreasing short-chain fatty acids available for absorption in the human gut comprising at least one of the following: a probiotic comprising an acetoclastic methanogen; a probiotic comprising a homo-acetogenic, an acetate-oxidizing bacterium that converts acetate to $H_2$; a miniaturized microbial electrolysis cell comprising anode-respiring bacteria, which oxidizes acetate and produces $H_2$; a prebiotic that enhances the growth or function of acetate-scavenging microbiota; an antibiotic.
2. The composition of claim 1, wherein the antibiotic is a selective antibiotic that targets $H_2$-oxidizing methanogens.
3. A method of managing obesity comprising administering to a patient in need thereof the composition of paragraph 1.
4. The method of paragraph 2, wherein the patient has undergone or will undergo gastric bypass surgery or gastric banding surgery.

We claim:

1. A method of managing obesity comprising administering to a patient in need thereof the composition for decreasing acetate available for absorption in the human gut, the composition comprising a component selected from the group consisting of:
   a probiotic comprising an acetoclastic methanogen; and
   a probiotic comprising a homo-acetogenic bacterium that is capable of reverse homoacetogenesis, wherein the homo-acetogenic bacterium converts acetate to $H_2$ and $CO_2$.

2. The method of claim 1, wherein the patient has undergone or will undergo gastric bypass surgery or gastric banding surgery.

3. The method of claim 1, wherein the composition comprises a probiotic comprising a homoacetogenic bacterium that is capable of reverse homo-acetogenesis, wherein the homo-acetogenic bacterium converts acetate to $H_2$ and $CO_2$.

* * * * *